US008951564B2

(12) United States Patent
Fattal et al.

(10) Patent No.: US 8,951,564 B2
(45) Date of Patent: Feb. 10, 2015

(54) GALENIC FORM SUITABLE FOR ABSORBING, IN A SPECIFIC MANNER, THE UNDESIRABLE MOLECULES IN THE DIGESTIVE TRACT

(75) Inventors: Elias Fattal, Paris (FR); Nicolas Tsapis, Paris (FR); Franceline Reynaud, Itajai (BR)

(73) Assignee: Centre National de la Recherche Scientifique—CNRS—, Paris (FR)

( * ) Notice: Subject to any disclaimer, the term of this patent is extended or adjusted under 35 U.S.C. 154(b) by 191 days.

(21) Appl. No.: 13/496,127

(22) PCT Filed: Sep. 22, 2010

(86) PCT No.: PCT/FR2010/051976
§ 371 (c)(1),
(2), (4) Date: May 29, 2012

(87) PCT Pub. No.: WO2011/036400
PCT Pub. Date: Mar. 31, 2011

(65) Prior Publication Data
US 2012/0231084 A1    Sep. 13, 2012

(30) Foreign Application Priority Data

Sep. 23, 2009   (FR) ..................................... 09 56542

(51) Int. Cl.
| | |
|---|---|
| A61K 9/14 | (2006.01) |
| A61K 9/16 | (2006.01) |
| A61K 9/60 | (2006.01) |
| A61K 9/64 | (2006.01) |
| A61K 31/722 | (2006.01) |
| A61K 33/26 | (2006.01) |
| A61K 33/30 | (2006.01) |
| A61K 33/34 | (2006.01) |
| A61K 45/06 | (2006.01) |

(52) U.S. Cl.
CPC ............... *A61K 9/1652* (2013.01); *A61K 9/143* (2013.01); *A61K 9/146* (2013.01); *A61K 31/722* (2013.01); *A61K 33/26* (2013.01); *A61K 33/30* (2013.01); *A61K 33/34* (2013.01); *A61K 45/06* (2013.01)
USPC ............ 424/489; 424/490; 424/491; 424/493

(58) Field of Classification Search
USPC .................................. 424/489, 490, 491, 493
See application file for complete search history.

(56) References Cited

U.S. PATENT DOCUMENTS

| | | | |
|---|---|---|---|
| 4,810,695 A | 3/1989 | Conti et al. | |
| 5,912,000 A * | 6/1999 | Podolski et al. | ........... 424/278.1 |
| 8,273,376 B2 * | 9/2012 | Andremont et al. | ........... 424/497 |
| 2005/0249716 A1 * | 11/2005 | Bourgeois et al. | ........... 424/94.6 |
| 2009/0162339 A1 | 6/2009 | Bourgeois et al. | |

FOREIGN PATENT DOCUMENTS

| | | |
|---|---|---|
| FR | 2 843 301 A1 | 2/2004 |
| WO | WO 2004/016248 A2 | 2/2004 |
| WO | WO 2006/122835 A1 | 11/2006 |
| WO | WO 2007/132022 A2 | 11/2007 |

OTHER PUBLICATIONS

Fattal et al., "Polysaccharide beads for colon delivery of antibiotic degrading enzymes", 15th Int'l Symposium on Microencapsulation, Parma (Italy), Sep. 18-21, 2005.*
C. Burger et al., "Cross-linking chitosan-Fe (III), an oral phosphate binder:studies in vitro and in vivo", International Journal of Pharmaceutics, Jul. 31, 2001, vol. 223, mo. 1-2, pp. 29-33.
M. Kara et al., "Clinical and chemical interactions between iron preparations and ciprofloxacin.", Br J Clin Pharmacol., Mar. 1991, vol. 31, No. 3, pp. 257-261.
L. Chow et al., "pH dependence of chitosan solubility determined using a titration method", The IADR/AADR/CADR $83^{rd}$ General Session, Mar. 10, 2005.
Arvand et al., "Simultaneous Determination of Zinc and Copper (II) with 1-(2-Pyridylazo)2-Naphthol in Micellar Media by Spectrophotometric H-Point Standard Addition Method," Chemistry Department, College of Science, Guilan University, Journal of Analytical Chemistry, vol. 62, No. 4, pp. 342-347 (2007).
Bartlett, "Antibiotic-Associated Diarrhea," N. Engl. J. Med., vol. 346, No. 5, pp. 334-339 (Jan. 31, 2002).
Bartlett, "Clostridium difficile Infection: Pathophysiology and Diagnosis," Seminars in Gastrointestinal Disease, vol. 8, No. 1, pp. 12-21 (Jan. 1997).
Broussignac, "Un haut polymere naturel peu connu dans l'industrie: Le Chitosane," Chimie et Industrie-Genie Chimique, vol. 99, No. 9, pp. 1241-1246 (May 1968).
Gupta et al., "Effects of degree of deacetylation and cross-linking on physical characteristics, swelling and release behavior of chitosan microspheres," Carbohydrate Polymers, vol. 66, pp. 43-54 (May 12, 2006).
Gupta et al., "Glutaraldehyde cross-linked chitosan microspheres for controlled release of centchroman," Carbohydrate Research vol. 342, pp. 2244-2252 (Jun. 12, 2007).
Holmberg et al., "Drug-Resistant Salmonella From Animals Fed Antimicrobials," N. Engl. J. Med., vol. 311, No. 10, pp. 617-622 (Sep. 6, 1984).
Khoder et al., "Removal of ciprofloxacin in simulated digestive media by activated charcoal entrapped within zinc-pectinate beads," Int. J. Pharm., 9 pages, (May 18, 2009).
Rapport, de l'Academie nationale de Pharmacie, "Medicaments et Environnement," pp. 23/103-25/103 (Sep. 2008).

* cited by examiner

*Primary Examiner* — Gina Justice
(74) *Attorney, Agent, or Firm* — Arent Fox LLP

(57) ABSTRACT

The present invention relates to a galenic form comprising particles capable of specifically adsorbing the undesirable molecules present in the digestive tract, to the method for preparing same and to the use thereof in particular for producing a medicine intended for preventing or treating undesirable effects linked to an imbalance of the intestinal and/or colonic flora that can result for example from treatment with antibiotics.

17 Claims, 12 Drawing Sheets

GALENIC FORM SUITABLE FOR ABSORBING, IN A SPECIFIC MANNER, THE UNDESIRABLE MOLECULES IN THE DIGESTIVE TRACT

CROSS-REFERENCE TO RELATED APPLICATIONS

This application is a National Stage entry of International Application No. PCT/FR2010/051976, filed Sep. 22, 2010, which claims priority to French Patent Application No. 0956542 filed Sep. 23, 2009, the disclosure of the prior application are incorporated in their entirety by reference.

TECHNICAL FIELD

The present invention relates to a galenic form comprising particles capable of specifically adsorbing the undesirable molecules present in the digestive tract, to the method for preparing same and to the use thereof in particular for producing a medicine intended for preventing or treating undesirable effects linked to an imbalance of the intestinal and/or colonic flora that can result for example from treatment with antibiotics.

In the description below, the references between square brackets ([ ]) refer back to the list of references provided at the end of the text.

PRIOR ART

The oral administration of medicines has an advantage compared with other routes of administration, for instance the parenteral route. Parenteral administration is generally painful and can cause complications. Furthermore, this route of administration requires suitable material, qualified personnel and aseptic conditions that prevent any exogenous introduction of microorganisms (bacteria, parasites, etc.).

Depending on the nature of the active ingredient, oral administration may be advantageous. This allows the active ingredients of medicines to pass through the stomach and then to be absorbed in the small intestine in order to diffuse throughout the organism and to treat the seat of infection for which they were administered. This is, for example, the case for antibiotics.

However, a fraction of the antibiotics ingested (the size of which varies with the specific characteristics of each type of antibiotic) is not absorbed and continues its progression to the colon before being eliminated in the faeces. These residual antibiotics are joined, in the small intestine, by a fraction of the antibiotics absorbed but which are re-excreted in the digestive tract by means of biliary elimination.

This fraction is of variable size depending on the metabolism and the routes of elimination of each antibiotic. Finally, for some antibiotics, a fraction of the dose absorbed is eliminated directly by the intestinal mucosa into the lumen of the digestive tract. Thus, whether the antibiotics were administered orally or parenterally, an active residual fraction is generally found in the digestive tract, in particular in the colon. This is true, to varying degrees, for the vast majority of families of antibiotics used in therapy, the only notable exception being the family of aminoglycosides for which intestinal excretion is negligible. For the other antibiotics, the intestinal excretion of a residual antibiotic activity will have various consequences, all detrimental. Indeed, in the colon, there is a complex (several hundred different bacterial species) and very dense (more than 10 million bacteria per gram of colonic content) bacterial ecosystem which will be affected by the arrival of the active residues of antibiotics.

The first consequence of the arrival of the active residues of antibiotics is that the numerous bacteria which populate the colon will be subjected to the action of the antibiotic. The vast majority of these bacteria are sensitive to the antibiotic and the action of the latter results in:

an imbalance in the flora that is thought to be the main cause of the commonplace diarrhea that sometimes follows the taking of antibiotics [1]. As a general rule, this diarrhea is not serious and quickly ceases, either spontaneously or once the treatment is stopped. It is, however, poorly appreciated by the patients and adds to the discomfort of the basic disease for which the antibiotic was prescribed. Pharmaceutical preparations based on replacement flora, or even the ingestion of yogurts, have been recommended for combating imbalances in colonic flora following treatment with antibiotics. None of these standpoints has, however, proven to be effective in a really convincing manner;

a disruption of the functions of resistance to colonization by exogenous bacteria (or "barrier effect") with the possibilities of an increased risk of infection, for example, salmonella food poisoning [2].

The second consequence of the arrival of a residual antibiotic activity on the colonic flora is the selection of microorganisms resistant to the antibiotic. These microorganisms may be of various types:

firstly, they may be pathogenic bacteria such as, for example, *Clostridium difficile*, a species capable of secreting toxins that cause dreadful colitis known as pseudomembranous colitis [3];

they may also be microorganisms that are not very pathogenic but the multiplication of which can lead to a neighboring infection (vaginal candidiasis or cystitis caused by resistant *Escherichia coli*);

finally, they may be commensal resistant bacteria that are nonpathogenic, but the multiplication and faecal elimination of which will increase the dissemination in the environment. As it happens, these resistant commensal bacteria can constitute an important source of resistance mechanisms for pathogenic species. This risk is currently considered to be a major one owing to the worrying nature of the evolution toward multi-resistance in numerous species pathogenic to humans.

For at least all these reasons, there remains a need to have a means for adsorbing and/or inactivating the undesirable residual molecules which arrive in the digestive tract.

The ingestion (intentional and/or accidental) of medicinal or domestic substances can constitute another case where the adsorption and/or inactivation of the undesirable molecules is desired. In France, each year, there are more than 130 000 cases of accidental or intentional poisoning with medicinal or domestic substances. 10% of these cases are fatal. Usually, patients are brought into the emergency department and subjected to various treatments. Although some toxic substances have specific antidotes, these are rare, their efficacy is often not proven and they are difficult to store. It should be noted that only 10% of poisonings can be treated in hospitals. In the majority of cases, clinicians only have solutions aimed at limiting the poisoning and ensuring survival of the patient: induced vomiting, gastric lavage, the use of activated carbon or Fuller's Earth, and symptomatic treatment. These treatments are often laborious, expensive and not without risks. In such cases, having a means for the emergency oral treatment of poisoning becomes a necessity. In the case of oral poisoning, the treatments currently in use to prevent the toxins from passing into the blood have recourse to either gastric lavage (which is recommended in the case of corrosive products and which has risks from a respiratory point of view), or activated carbon (the efficiency of which has not been completely demonstrated and the use of which consequently varies depending on the hospital).

Moreover, the residues of medicines, when they are not completely degraded in the body, are excreted in the faeces and the urine in their initial form or in the form of one or more metabolites. It is today considered that the environmental impact of medicines discharged in this way into the ecosystem will be high.

Galenic forms based on the release of enzymes capable of degrading antibiotics in the colon have been proposed in order to reduce the presence of undesirable molecules in the digestive tract and/or the discharging thereof into the ecosystem. However, these galenic forms do not always exhibit the desired stability throughout the digestive tract, which can lead to the premature release of the active ingredient.

Other galenic forms which allow adsorbents of the carbon, bentonite, etc, type to be delivered to the colon have also been developed. The major drawback of this type of system lies in the lack of specificity of the adsorption with respect to the molecules adsorbed.

Whether it is a question of toxic substances, medicine residues or metabolites thereof, or residual antibiotics capable of modifying the colonic flora and of leading to the emergence of resistance, there is a real need to develop a galenic form for eliminating the undesirable molecules in the digestive tract by adsorption, which overcomes the deficiencies, drawbacks and obstacles of the prior art.

In particular, there is a real need to develop a galenic form which is simultaneously simple to prepare, readily reproducible and transposable to a larger scale, making it possible to specifically adsorb the undesirable molecules present in the digestive tract, in particular in the small intestine and/or the colon.

The document Journal of Colloid and Interface Science 330 (2009), pages 29-37, describes magnetic iron oxide nanoparticles coated with chitosan and modified with ketoglutaric acid, intended to trap the $Cu^{2+}$ in wastewater.

DESCRIPTION OF THE INVENTION

The objective of the present invention is specifically to meet this need by providing galenic forms comprising particles capable of specifically adsorbing the undesirable molecules present in the digestive tract, said particles comprising a cationic polymer associated with at least one metal ion.

It involves a galenic form comprising particles capable of specifically adsorbing undesirable molecules present in the digestive tract, said particles comprising (i) a cationic polymer chosen from polyethyleneimine, polylysine, polyarginine and cationic polysaccharides, associated with (ii) at least one metal ion chosen from alkaline earth metals, transition metals or a mixture thereof, said cationic polymer and said at least one metal ion forming a complex.

The components of the digestive tract can be classified essentially in three parts: the esophagus, the stomach and intestines. The intestines in turn comprise the small intestine, the large intestine or colon and the rectum. The galenic forms according to the invention can be used for the adsorption of undesirable molecules present in all the components of the digestive tract.

In one particular embodiment, the invention relates to the galenic forms comprising particles capable of specifically adsorbing the undesirable molecules present in the intestines, more particularly in the small intestine and/or the colon.

For the purpose of the invention, the term "undesirable molecules" is intended to mean the molecules undesirable for the organism and/or the ecosystem that are located in the digestive tract, for example in the intestines, in particular in the small intestine and/or the colon. In this respect, undesirable molecules that may be mentioned, in a non-limiting manner, include:
  domestic toxic substances such as, for example, detergents, substances which are part of the composition of household pesticides, bleach, stain-removal agents, rust-proofing agents (such as Rubigine), descaling agents;
  medicine residues or metabolites of medicines which are intentionally and/or accidentally ingested;
  medicine residues or metabolites of the medicine most widely used in human or veterinary medicine and which are found in water, for instance those indicated in the report by the Academy of Pharmacy [5];
  residual antibiotics, for instance beta-lactam antibiotics, quinolones, in particular fluoroquinolones, aminoglucosides, macrolides, sulfamides, antitubercular agents, and tetracyclines.

The galenic forms according to the invention comprise particles which are capable of specifically adsorbing the undesirable molecules contained in the digestive tract, for example in the intestines, in particular in the small intestine and/or the colon. In the context of the invention, the term "specific" means that the adsorption takes place in a specific manner with respect to one type of given molecule. In other words, the galenic forms according to the invention are capable of distinguishing the undesirable molecules to be adsorbed from the other molecules present in the digestive tract, advantageously in the intestines and in particular in the small intestine and/or the colon.

As indicated, the galenic forms according to the invention comprise particles capable of specifically adsorbing the undesirable molecules contained in the digestive tract. These particles comprise a cationic polymer associated with at least one metal ion.

The cationic polymer may, for example, be chosen from the group comprising polyethyleneimines, polylysines, polyarginines and cationic polysaccharides.

In one particular embodiment, the cationic polysaccharides may be polysaccharides comprising amine groups. The cationic polysaccharides may, for example, be DEAE dextran (or diethylaminoethyl dextran) or chitosan. In another particular embodiment according to the invention, the cationic polysaccharide is chitosan.

Chitosan is a polysaccharide composed of the random distribution of $\beta$(1-4)-linked D-glucosamine (deacetylated unit) and of N-acetyl-D-glucosamine (acetylated unit). Chitosan is produced by chemical deacetylation (in alkaline medium) or enzymatic deacetylation of chitin, which is one of the main components of the exoskeleton of insects and other arthropods (crustaceans) or the endoskeleton of cephalopods (squid, etc) or else the wall of fungi. Unlike chitin, chitosan is insoluble in an alkaline medium and neutral medium but soluble in an acidic medium.

The border between chitosan and chitin corresponds to a degree of acetylation (DA) of 50%; below this, the compound is called chitosan, above this, chitin. The degree of acetylation (DA) is the percentage of acetylated units relative to the number of total units; it can be determined by Fourier transform infrared (FT-IR) spectrometry or by titration with a strong base. It is important to make the distinction between the degree of acetylation (DA) and the degree of deacetylation (DD), one being the inverse of the other, i.e. for example chitosan, which has a DD of 70%, has 30% of acetylated groups and 70% of amine groups on its chains.

The chitusan may advantageously have a deacetylation rate of at least 50%, for example between 55 and 90%, for example between 70 and 80%.

The particles comprising a cationic polymer associated with at least one metal ion can have a diameter that can range from 0.01 µm to 1 mm, for example from 0.01 to 100 µm, for example from 0.1 to 10 µm.

The metal ion(s) can be chosen from alkaline earth metals, transition metals, or a mixture thereof. The metal ion(s) can be chosen from the group comprising, for example, iron, copper, zinc or a mixture thereof.

Said cationic polymer and said metal ion(s) together form a complex. For the purpose of the invention, a complex denotes a polyatomic structure consisting of a metal ion associated with at least one chemical group capable of delocalizing a part of its electron density on the metal ion, thus forming coordination bonds therewith. The chemical group may be, for example, an amine group.

For 1 g of cationic polymer, the amount of metal ion(s) associated may be from 1 to 300 mg, for example from 10 to 200 mg.

When the cationic polymer is chitosan, for 1 g of chitosan, the amount of metal ion(s) associated may be from 20 to 200 mg, for example from 35 to 135 mg, or even from 40 to 135 mg.

Depending on the nature of the metal ion, and the nature of the chemical groups present in the undesirable molecules, the metal ion may specifically form a complex with said molecules.

According to one embodiment of the invention, when the undesirable molecules are antibiotics, the galenic forms comprise particles that may contain, in addition, at least one agent capable of inactivating said antibiotics. The antibiotics may be, for example, quinolones, aminoglucosides, beta-lactam antibiotics, macrolides, sulfamides, antitubercular agents, and tetracyclines. Said agent may be an enzyme. By way of example, mention may be made of beta-lactamases and/or erythromycin esterases. Those skilled in the art will know to choose the suitable agent according to the antibiotic to be activated.

As already indicated, the galenic forms according to the invention comprise particles capable of specifically adsorbing the undesirable molecules present in the digestive tract. In order to further increase the stability of the particles along the digestive tract and in order to avoid premature adsorption of molecules, it is possible to reinforce the particles by crosslinking them. Thus, in one particular embodiment of the invention, the galenic forms comprise particles in crosslinked form. The particles can then have a degree of crosslinking ranging from 0 to 100%, for example from 1 to 99%, for example 10 to 80%. When the cationic polymer is a polysaccharide comprising amine groups the crosslinking can advantageously take place via said amine groups.

The degree of crosslinking can then be defined as the percentage of free amine groups crosslinked by the crosslinking agent, relative to the amine groups initially free.

The degree of crosslinking of the particles can be determined by infrared spectroscopy, or else by titration [4] and [6].

As crosslinking agent, mention may be made, for example, of glutaraldehyde, glyceraldehyde, formaldehyde, epichlorohydrin and tripolyphosphate.

According to another particular embodiment of the invention, the galenic forms comprise particles as described previously, encapsulated in pectin beads. The term "pectin beads" is intended to mean particles of which the average diameter is between 0.2 and 3 mm, for example from 0.5 to 1.7 mm, for example from 1 to 1.5 mm, obtained by ionic gelling of drops of a solution of pectin in a bath of an aqueous solution containing multivalent cations, for example divalent or trivalent cations [9]. Among these multivalent ions, mention may be made, for example, of calcium ions, zinc ions, aluminum ions, iron ions or magnesium ions.

For the purpose of the invention, the term "pectin" is intended to mean methylated, non-methylated, amidated or non-amidated pectin. More particularly, the pectin beads are zinc pectinate or calcium pectinate beads.

Pectin has the advantage of being of natural origin, devoid of toxicity and able to be specifically degraded by pectinolytic enzymes present in the colon. Once they have arrived in the colon, the beads degrade so as to release the particles which can then adsorb the undesirable molecules, such as, for example, fluoroquinolones. The encapsulation thus makes it possible to further reinforce the stability of the particles and further promote release in the colon.

In this embodiment, in the galenic forms, the concentration of pectin is from 5 to 95% by weight, for example from 25 to 50% by weight, relative to the total weight of the galenic form, and that of the cationic polymer-metal ion(s) association is from 5 to 95% by weight, for example from 25 to 50% by weight, relative to the total weight of the galenic form.

Still in this embodiment, the pectin beads may be spherical in shape and may have a diameter that can range from 0.2 to 3 mm, for example from 0.5 to 1.7 mm, for example from 1 to 1.5 mm.

In another particular embodiment of the invention, the particles, optionally encapsulated in pectin beads, may be coated with:
- a cationic polymer chosen from the group comprising polyethyleneimine, polylysine, polyarginine, DEAE dextran (or diethylaminoethyl dextran) and chitosan;
- a cellulosic polymer chosen from the group comprising hydroxypropylcellulose, hydroxyethylcellulose, hydroxymethylcellulose, hydroxypropylmethylcellulose, hydroxypropylmethylcellulose acetate succinate, hydroxypropylmethylcellulose phthalate, methylcellulose, ethylcellulose, cellulose acetate, cellulose acetate phthalate, cellulose acetate trimellitate, and sodium carboxymethylcellulose;
- a polymer of acrylic acid, of methacrylic acid, of ethyl acrylate, of ethyl acrylate, of methyl methacrylate and/or of ethyl methacrylate, chosen from the group comprising the Eudragits®, in particular Eudragit® NE, RL and RS, Eudragit® L30D-55 and L100-55, Eudragit® L100, Eudragit® S and Eudragit® FS30D;
- a vinyl polymer chosen from the group comprising polyvinylpyrrolidone, vinyl acetate, vinyl acetate phthalate, vinyl acetate-crotonic acid, and ethylene-vinyl acetate.

As already indicated, the galenic forms of the invention comprise optionally encapsulated and/or coated particles capable of specifically adsorbing the undesirable molecules present in the digestive tract.

The coating makes it possible to further reinforce the stability of the optionally encapsulated particles and to further promote release in the digestive tract, advantageously in the intestines, in particular in the small intestine and/or the colon.

In the case of particles encapsulated in pectin beads, for example zinc pectinate beads, then coated with a polymer, for example a polymer of the Eudragit family, the coating can dissolve in the small intestine and the zinc pectinate matrix is then degraded by the pectinolytic enzymes present in the colon, so as to release the chitosan-metal particles, which particles can then adsorb the undesirable molecules, for instance antibiotics.

A subject of the present invention is also a method for preparing the galenic forms as previously described, in which:

(a) a cationic polymer chosen from polyethyleneimine, polylysine, polyarginine and cationic polysaccharides is dissolved in an aqueous solution of a metal salt or of a mixture of metal salts, under pH conditions<7, advantageously at a pH of between 1 and 6.8, even more advantageously at a pH between 1.2 and 6, in such a way that the metal ions of said salt or said mixture of salts associate with said cationic polymer so as to form a complex;

(b) the solution obtained in (a) is subjected to spray-drying, so as to obtain particles of said complex;

(c) crosslinking of the particles obtained in step (b) is optionally carried out in an organic solvent in the presence of a crosslinking agent.

According to one embodiment, the cationic polymer is chosen from cationic polysaccharides and in particular is chitosan.

In step (a), the cationic polymer can be dissolved at a concentration of between 0.2 and 10% (w/v) in an aqueous solution of a metal salt or of a mixture of metal salts at a concentration of between 0.01 M and 1 M, for example 0.1 M. As metal salt, mention may be made, for example, of copper sulfate, nitrate, chloride or acetate, iron sulfate, nitrate, chloride or acetate and zinc sulfate, nitrate, chloride or acetate.

The dissolution is carried out at a pH <7, for example at a pH of 6.8, 6, 5 or 2. The dissolution time depends on said pH: the closer the pH is to 7, the longer the dissolution time (approximately a few hours) and, conversely, the closer the pH is to 1, the shorter the dissolution time (approximately one hour). The resulting solution can be left to stir for a period between 1 h and 24 h, for example 12 h, at ambient temperature (25° C.). At the end of this step, a solution is obtained in which the metal ions are associated with the cationic polymer.

In step (b), the solution obtained in (a) is subjected to spray-drying. Spray drying is a technique for removing water which consists in spraying a product in liquid solution or suspension form, in a stream of hot gas (air or an inert gas). At the end of this step, the particles of cationic polymer obtained are in the form of powder with in particular an improved flowability facilitating handling thereof and assaying thereof. Since spray-drying is a well-known process, those skilled in the art will be able to determine the parameters (for example the drying speed, the temperature of the product to be dried, the gas input and output temperature, etc.) for optimum implementation.

In step (c), in order to carry out the crosslinking of the particles, the particles obtained in step (b) are suspended in an organic solvent and a crosslinking agent is introduced therein. The organic solvent may be chosen, for example, from methanol, ethanol, pyridine, acetone, acetic acid, DMSO and dichloromethane. The reaction medium may or may not contain water.

The suspension of particles can be incubated with stirring with the crosslinking agent at ambient temperature (25° C.) for a period of between 10 min and 24 h, for example 4 h. The crosslinked or non-crosslinked particles can then be filtered and washed in a mixture of water and water-miscible organic solvent, for instance a water-ethanol mixture, in order to remove the metal ions and also the excess crosslinking agent. The particles can then be dried under vacuum or in an incubator for a period of between 1 h and 48 h, for example 24 h. The temperature of the incubator may be between 25 and 100 degrees Celsius, for example 37° C.

In order to prepare the encapsulated particles, after step (b), or after step (c), the particles are first suspended in water. The concentration of the particles in the suspension can range from 0.1 to 10% (w/v), for example 3%. A solution of pectin, having a concentration that can range from 0.1 to 10% (w/v), for example 3%, is then mixed with the suspension of chitosan-metal particles. The mixture is then formulated by causing drops of this mixture to drop into a bath containing multivalent cations, for example a 12% (w/v) zinc acetate solution. Ionic gelling is obtained by leaving the drops of the mixture to stir in the solution of multivalent ions for a period of time of between 1 min and 24 hours, for example between 5 min and 1 hour, for example between 10 and 30 min. The pectin beads containing particles according to the invention thus obtained are then filtered and rinsed several times in water, advantageously ultrapure water (conductivity 18.2 Megaohms·cm, Synergy purification system from Millipore, France), for example between 0 and 10 times, for example between 1 and 4 times. The pectin beads containing particles according to the invention thus obtained are optionally dried, for example in an incubator for a period of between 1 min and 48 hours, for example between 10 min and 24 hours, for example 12 hours. The temperature of the incubator may be between 25 and 100 degrees Celsius, for example 37° C.

The pectin beads containing particles according to the invention thus obtained can also be lyophilized.

As already indicated, the optionally encapsulated particles can further be coated with a polymer as defined previously. To this effect, the coating can be carried out with a solution or a suspension of Eudragit® for example using a fluidized air bed or a coating turbine. These techniques are well known to those skilled in the art in the field of galenics.

Another subject of the present invention relates to the galenic forms as previously described as a medicine. Said medicine may also comprise components well known to those skilled in the art in the pharmaceutical field, such as stabilizers, emulsifiers, tonicity agents, preservatives, dyes, excipients, binders or lubricants.

The galenic forms according to the invention can be used for preventing or treating the undesirable effects linked with an imbalance of the intestinal and/or colonic flora following treatment with antibiotics.

Another subject of the invention consists of the use of a galenic form according to the invention for producing a medicine intended for preventing or treating the undesirable effects linked with an imbalance of the intestinal and/or colonic flora following treatment with antibiotics for example.

The galenic forms of the invention can be administered in any oral forms, in particular in the form of gel capsules and capsules. The galenic forms can be administered before, during or after the administration of an antibiotic.

Other advantages may also become apparent to those skilled in the art on reading the examples below, illustrated by the appended figures, which are given by way of illustration.

(top right), of chitosan-Cu (bottom left), of chitosan-Zn (bottom right) after crosslinking with glutaraldehyde and cleaning.

Figure 4:
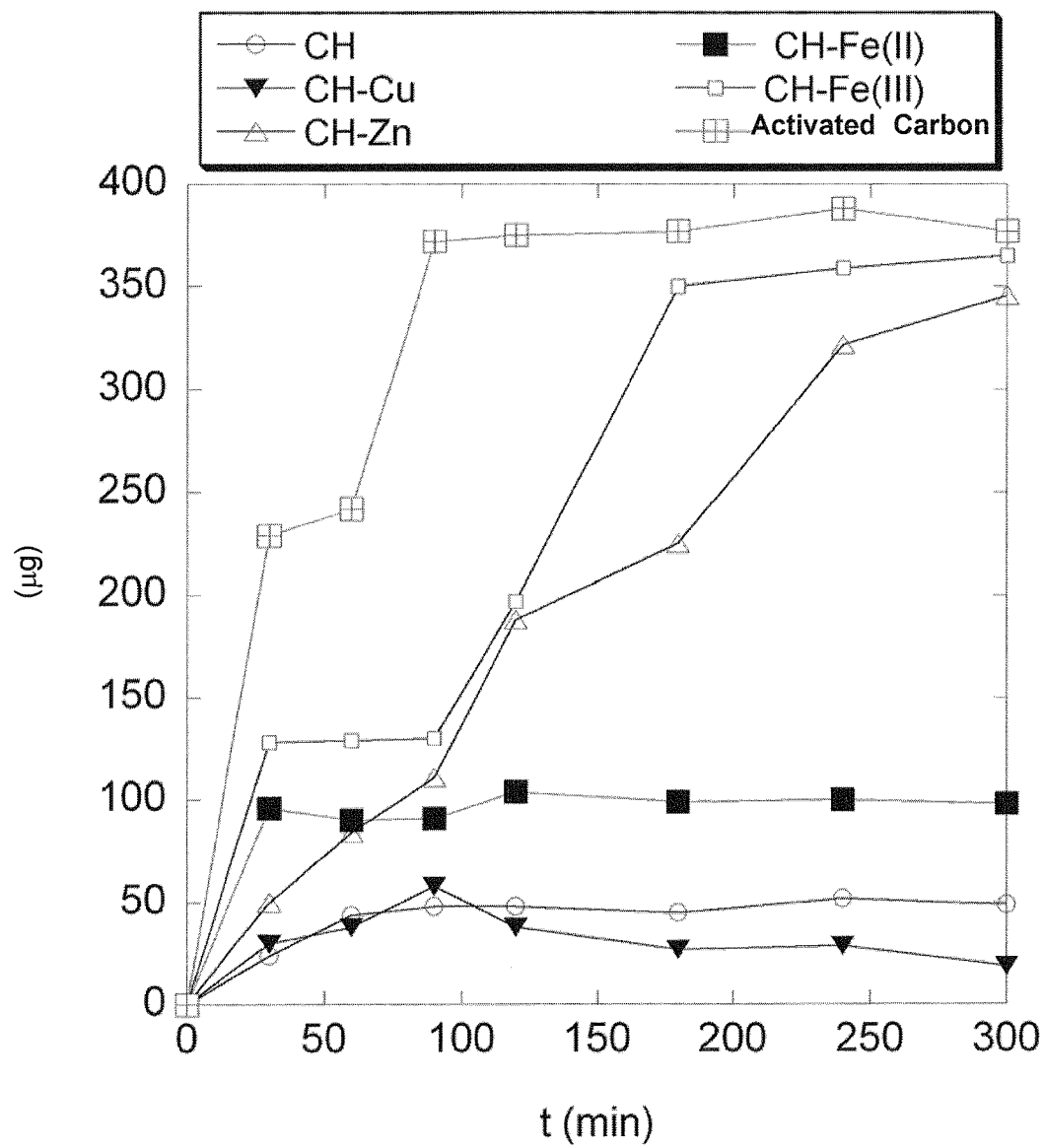

FIG. 4 represents the kinetics of adsorption of ciprofloxacin at 400 μg/ml by the various crosslinked particles in simulated colonic medium. For comparison, the kinetics obtained with active carbon under the same conditions have been added.
CH=chitosan particles,
CH—Cu=chitosan-copper particles,
CH—Zn=chitosan-zinc particles,
CH—Fe(II)=chitosan-iron(II) particles,
CH—Fe(III)=chitosan-iron(III) particles,
CH—Cu=chitosan-copper particles.

The Y-axis corresponds to the amount of ciprofloxacin adsorbed (expressed in μg) by the particles.

Figure 5:
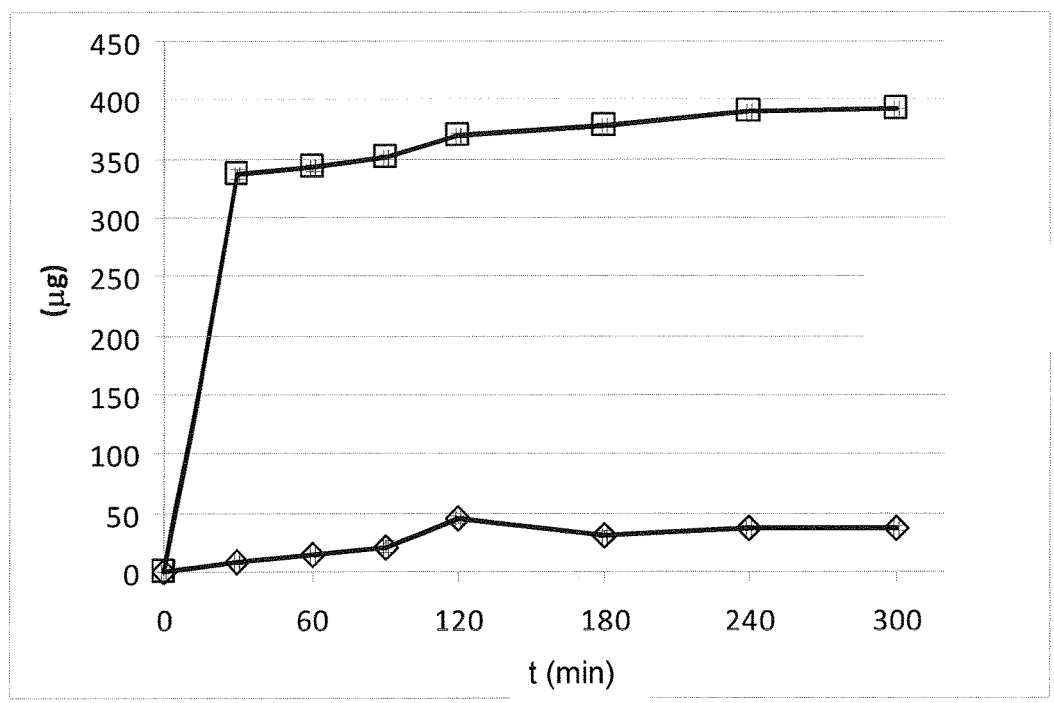

FIG. 5 represents the kinetics of adsorption of hydrocortisone by the active carbon and chitosan-Fe(III) particles. The diamonds represent the chitosan-Fe(III) particles and the squares represent the active carbon. The Y-axis corresponds to the amount of hydrocortisone adsorbed (expressed in μg) by the particles. These results confirm the nonspecificity of the chitosan-Fe(III) particles for hydrocortisone.

Figure 6:
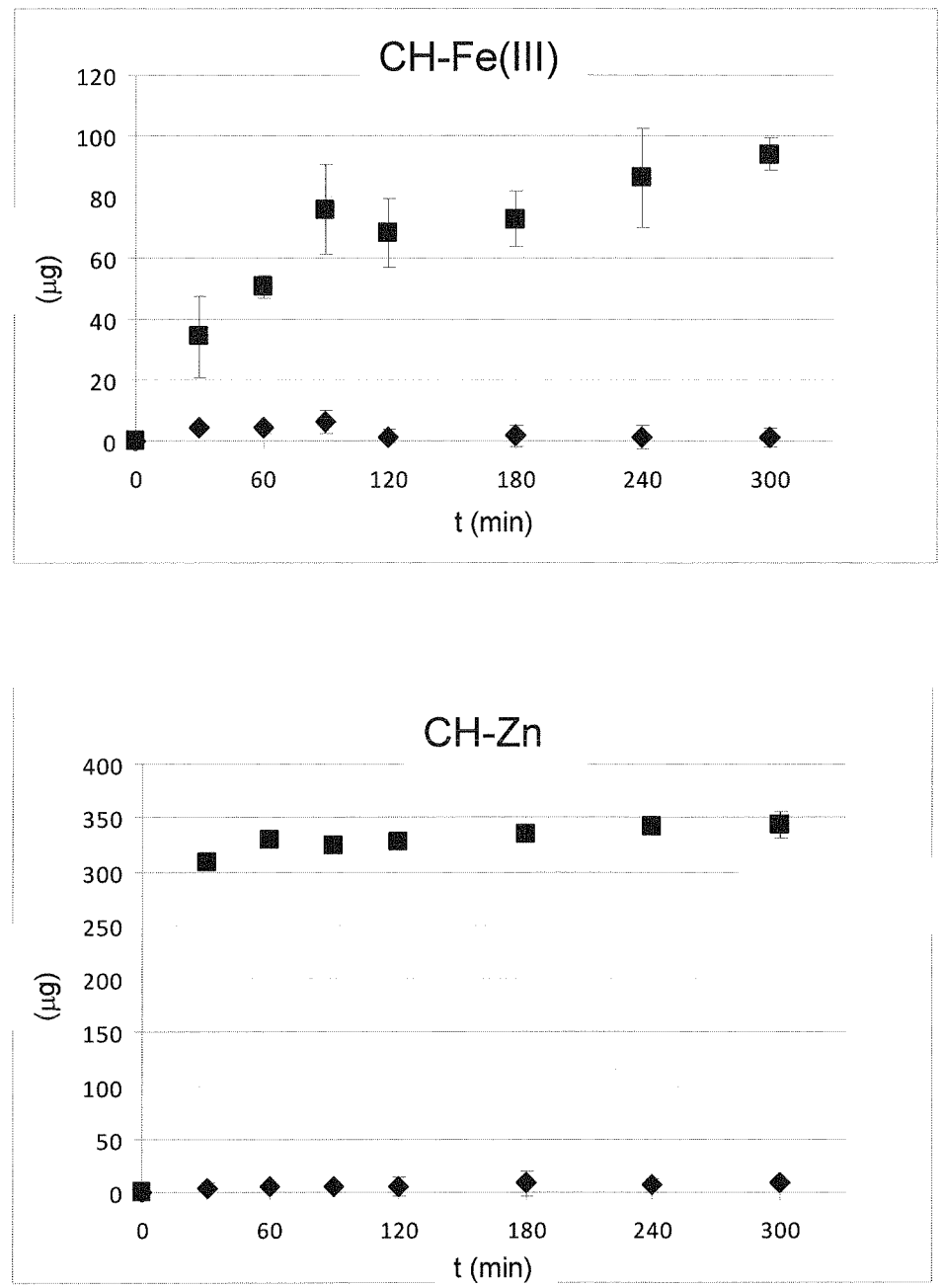

FIG. 6 represents the kinetics of adsorption of ciprofloxacin under conditions of competition with nimesulide, for chitosan-Fe(III) and chitosan-Zn particles. The diamonds represent nimesulide and the squares ciprofloxacin. The y-axis corresponds to the amount of molecule adsorbed (expressed in pg) by the particles. These results confirm the specificity of the chitosan-Fe(III) and chitosan-Zn particles for ciprofloxacin.

Figure 7:
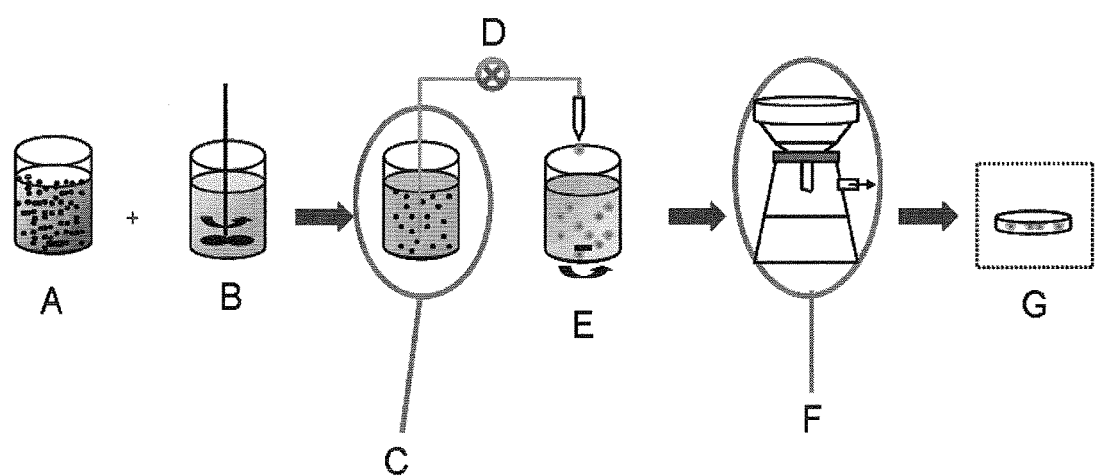

FIG. 7 represents the method for producing the pectin beads containing the particles according to example 6.
A=suspension of particles
B=solution of pectin
C=mixture of pectin/particles
D=syringe driver
E=50 ml of 12% (w/v) zinc acetate solution
F=washing for 1 min in 50 ml of water
G=drying.

Figure 8:
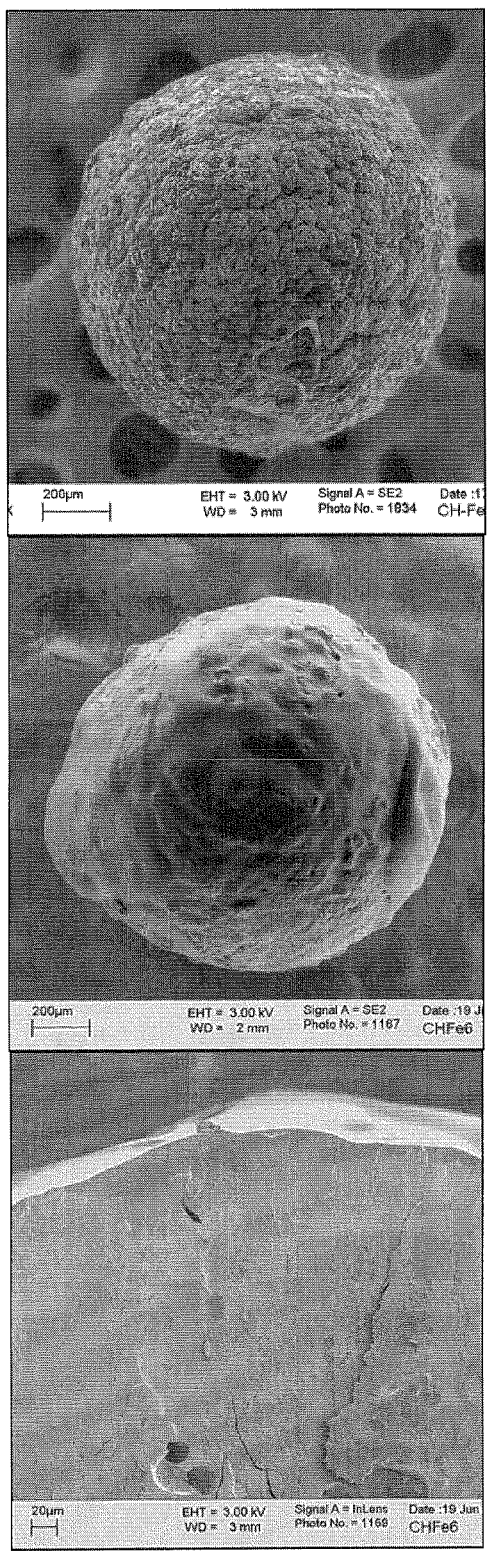

FIG. 8 represents the scanning electron microscopy images of a bead of zinc pectinate encapsulating the chitosan-Fe(III) particles (top). The image in the middle corresponds to a bead coated with Eudragit® RS, and that at the top corresponds to a section of a coated bead: the layer of Eudragit® can be clearly distinguished.

Figure 9:
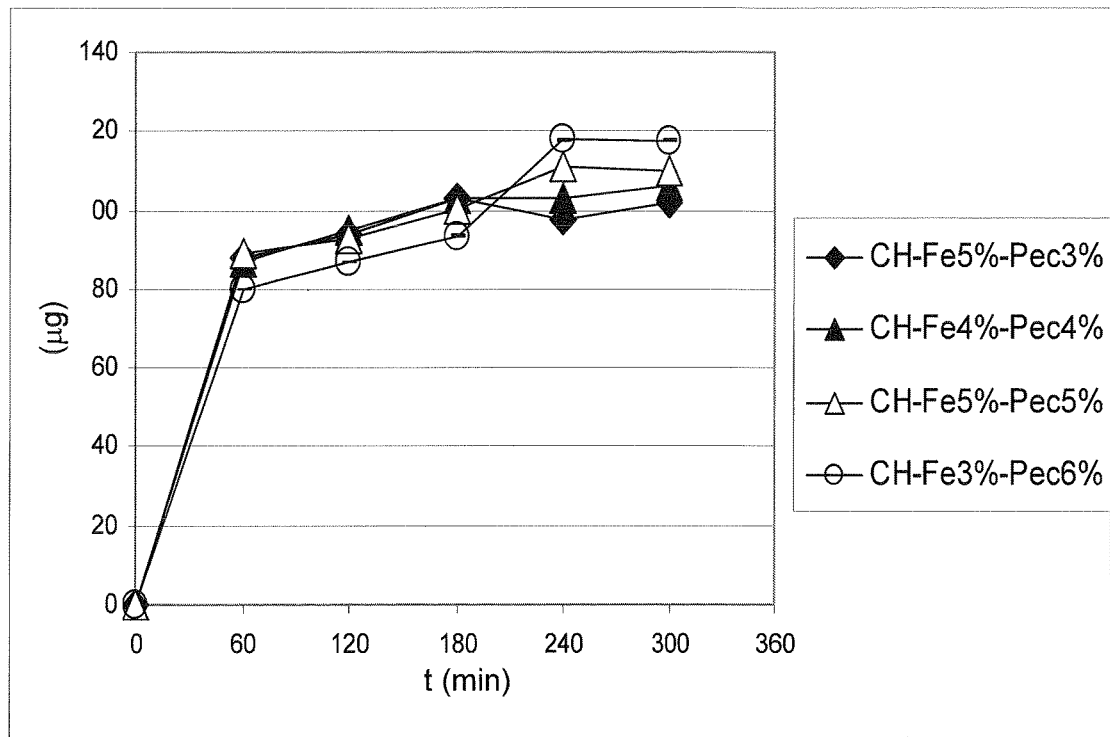

FIG. 9 represents the kinetics of adsorption of the beads encapsulating the chitosan-Fe(III) {or CH—Fe(III)} particles in the simulated intestinal medium (SIM). The beads are not coated with Eudragit®.

Figure 10:
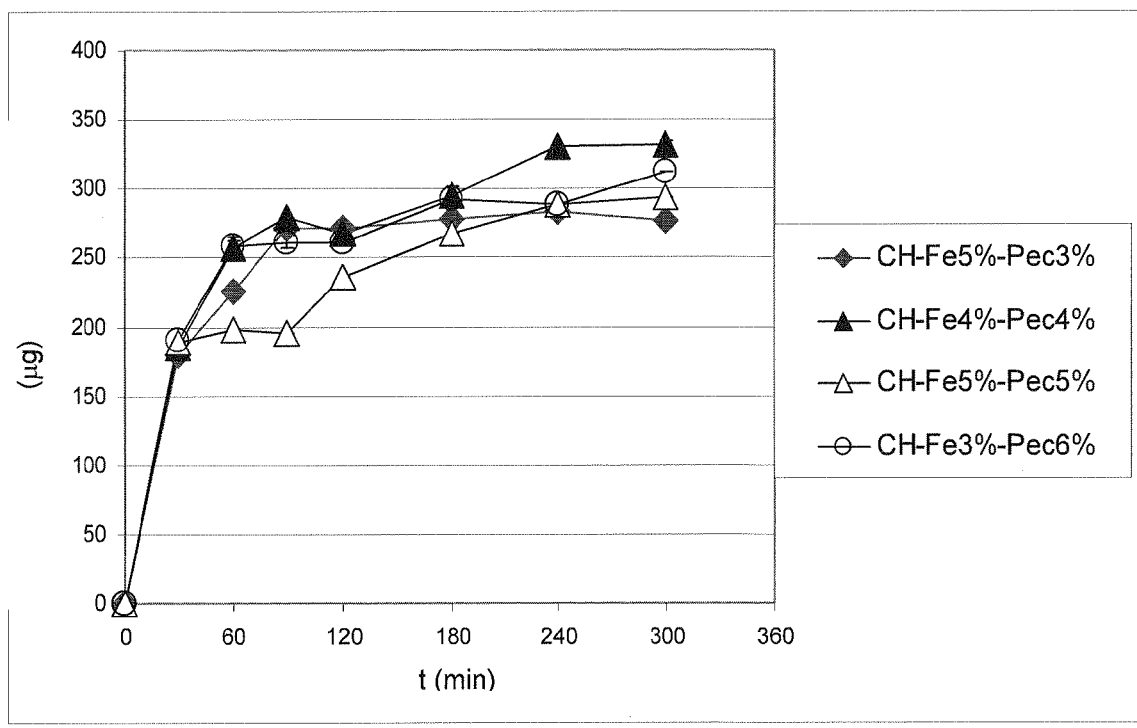

FIG. 10 represents the kinetics of adsorption of the beads encapsulating the chitosan-Fe(III) {or CH—Fe(III)} particles in the simulated colonic medium (SCM). The beads are not coated with Eudragit® and were preincubated in the SIM containing ciprofloxacin at 400 μg/ml. The y-axis corresponds to the amount of ciprofloxacin adsorbed (expressed in μg) by the encapsulated particles.

Figure 11:
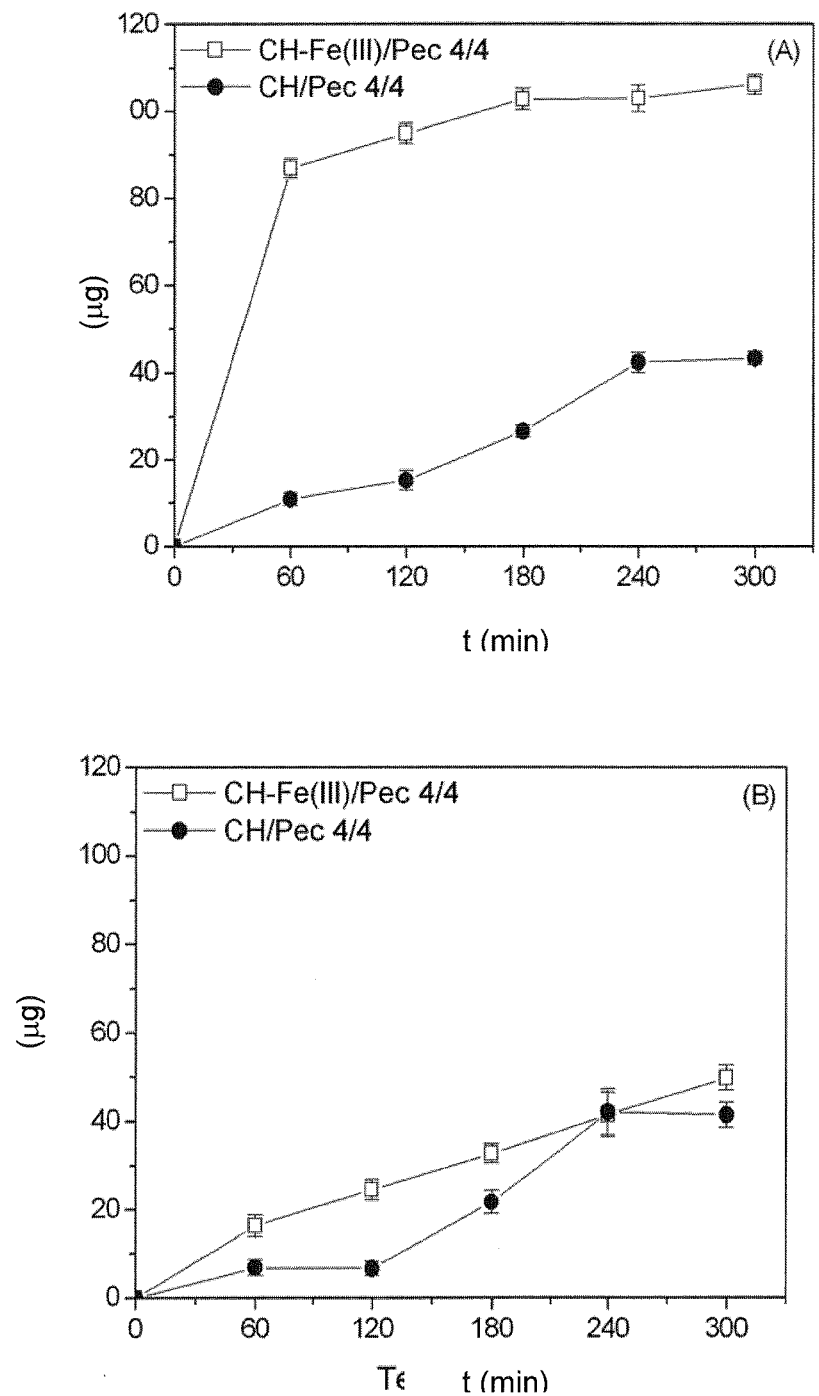

FIG. 11 represents the kinetics of adsorption of ciprofloxacin at 400 μg/ml by uncoated beads (A) and beads coated with Eudragit® (B) in the SIM. The y-axis corresponds to the amount of ciprofloxacin adsorbed (expressed in μg) by the encapsulated particles.

Figure 12:
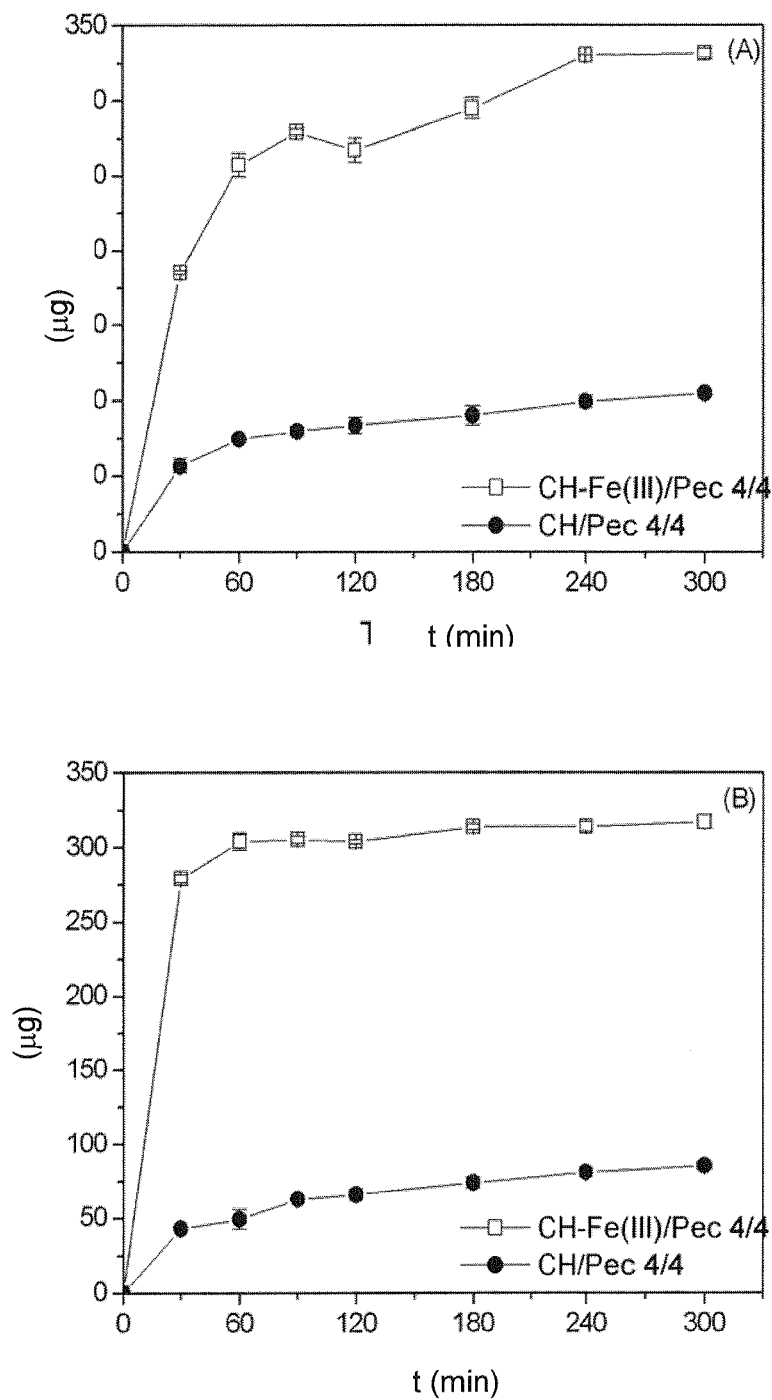

FIG. 12 represents the kinetics of adsorption of ciprofloxacin at 400 μg/ml by the uncoated beads (A) and beads coated with Eudragit® (B) in the SCM, after preincubation in the SIM. The y-axis corresponds to the amount of ciprofloxacin adsorbed (expressed in pg) by the encapsulated particles.

EXAMPLES

Example 1

Complexation of Metal Ions with Chitosan

The chitosan (low molecular weight), the zinc acetate dihydrate and the ciprofloxacin come from Fluka (Switzerland). The glutaraldehyde, the copper(II) sulfate and the sodium acetate come from Prolabo (Paris-France). The iron(II) chloride comes from Acros Organic (Geel, Belgium). The hydroxyethylpiperazine-ethanesulfonic acid (HEPES), the 1-(2-pyridylazo)-2-naphthol (PAN), the ammonia buffer (pH 10) for complexometry, the hydroxylamine hydrochloride, the 1,10-phenanthroline and the iron(III) nitrate were purchased from Sigma-Aldrich (France). The HPLC-grade solvents come from Carlo Erba (Italy).

Figure 1:
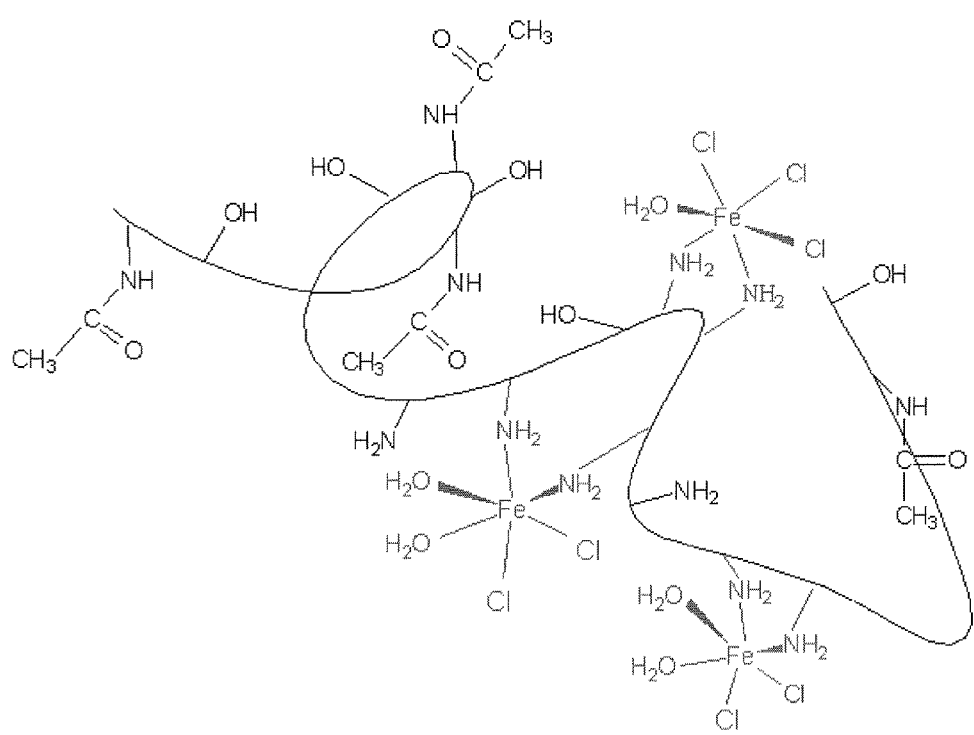
FIG. 1 represents a chitosan-Fe(III) complex.

The chitosan was complexed with the metal ions (copper, iron(II), iron(III) and zinc) by dissolving 1 g of chitosan in 100 ml of an aqueous solution of metal ions at 0.1 M ($CuSO_4$, $FeCl_2$, $Fe(NO_3)_3$ and $Zn(CH_3COO)_2$). The solutions were then stirred for 12 hours at ambient temperature (25° C.). The complexation occurred via the "free" amine groups of chitosan according to FIG. 1. The metal ions are added in slight excess relative to the number of "free" amine groups of the chitosan.

Example 2

Preparation of the Galenic Forms

The chitosan-metal ion (copper, iron(II), iron(III) and zinc) complexes prepared in example 1 are subjected to spray-drying in order to form the particles. 200 ml of the solution of complex are spray-dried by means of a B191 spray-dryer apparatus (Büchi, France). The nozzle has an internal diameter of 0.7 mm and operates with compressed air at a flow rate of 600 l/h. The input temperature of the apparatus is fixed at 150° C. The output temperature is between 75 and 100° C. The flow rate of the pump bringing the solution to be spray-dried is fixed at 5 ml/min. The particles are recovered in the form of powder in the cyclone of the apparatus.

Figure 2:
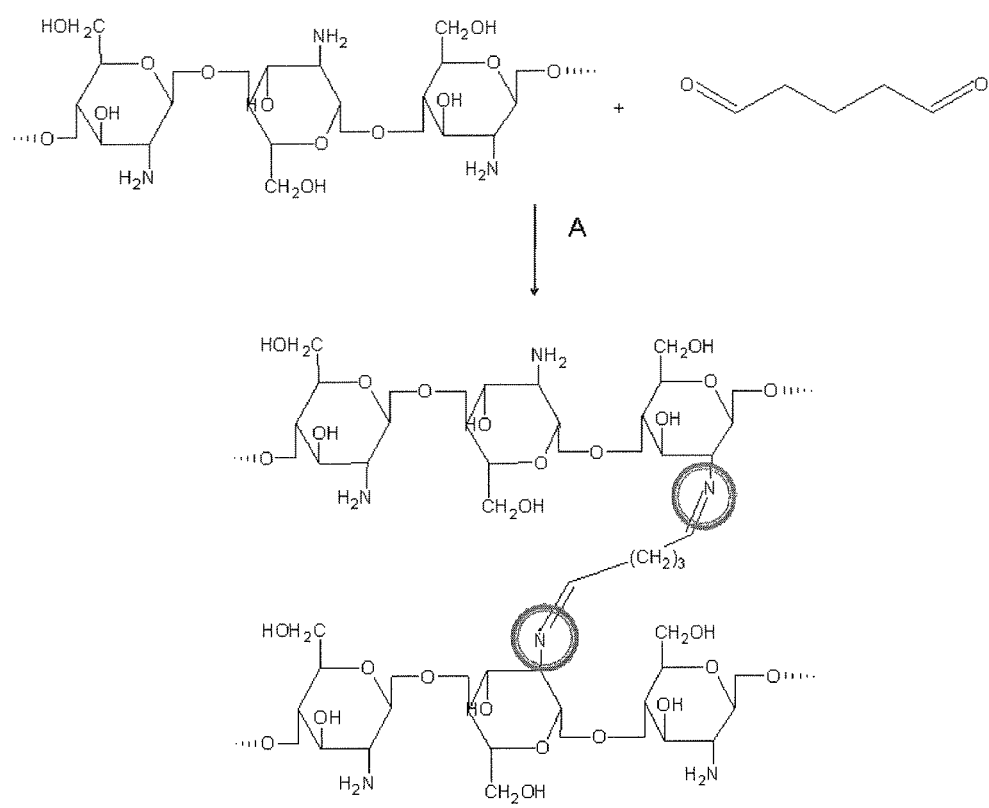
FIG. 2 represents the reaction scheme for crosslinking chitosan with glutaraldehyde. Step A which corresponds to a crosslinking step takes place with stirring for 4 hours in acetone.

The particles are then suspended in acetone with glutaraldehyde (chitosan/glutaraldehyde molar ratio 1:1) for four hours with magnetic stirring so as to obtain crosslinking (FIG. 2). The particles are then thoroughly rinsed with an ethanol/water mixture (2/1, v/v) so as to remove the glutaraldehyde and the residual metal ions. The particles cleaned were finally dried under vacuum for 24 h.

Figure 3:
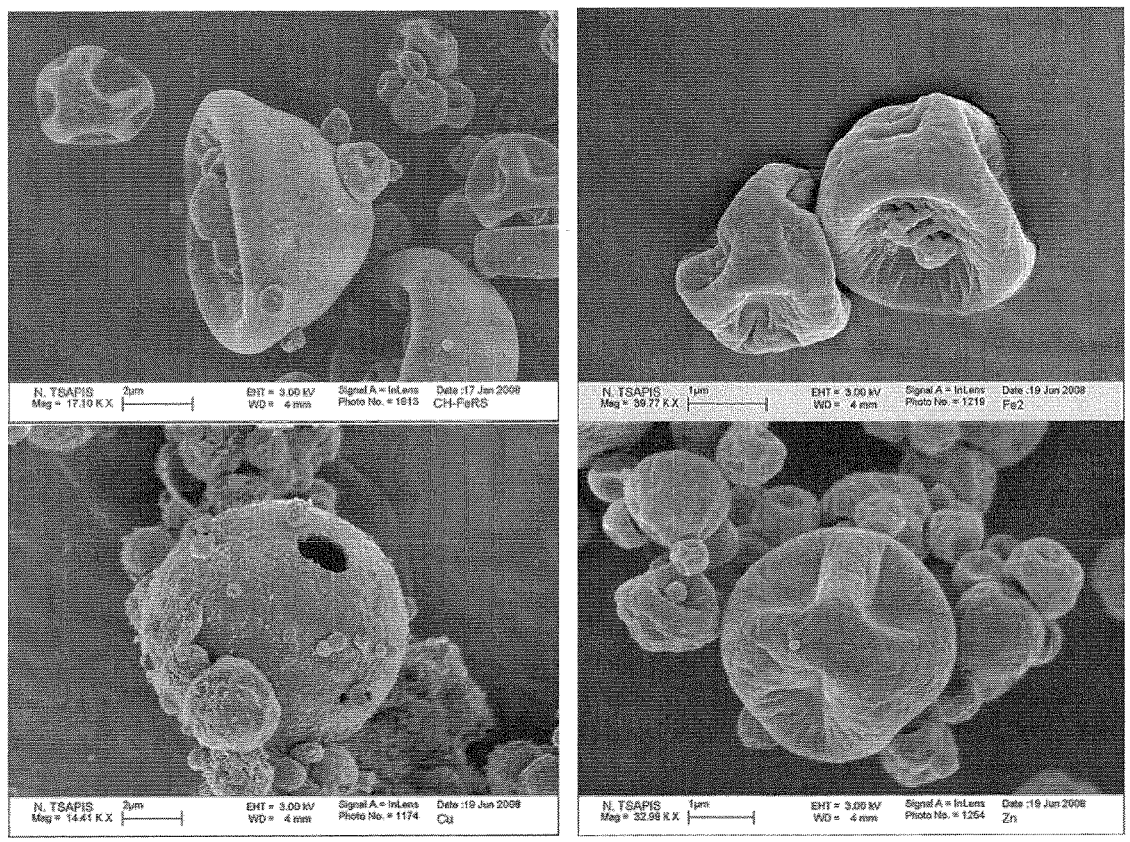
FIG. 3 represents the scanning electron microscopy images of particles of chitosan-Fe(III) (top left), of chitosan-Fe(II)

The scanning electron microscopy observations were carried out with an LEO 1530 microscope (LEO Electron Microscopy Inc, Thornwood, N.Y.) at an acceleration voltage of 3 kV and a current of 0.5 mA. The particles were deposited on a conductive adhesive strip (Euromedex, France) before being metalized with 2 nm of a layer of platinum-palladium alloy with a Cressington 208HR apparatus (USA). The scanning electron microscopy shows that the particles have a relatively smooth surface (FIG. 3).

In the particles, the amount of metal ions associated with the chitosan was assayed by colorimetry: 131 mg Fe(III)/1 g chitosan; 45 mg Fe(II)/1 g chitosan and 87 mg Zn/1 g chitosan. More particularly, the amount of iron (Fe(II) or Fe(III)) was assayed using 1,10-phenanthroline by spectrophotometry: the particles of CH—Fe(II) or of CH—Fe(III) were first subjected to hydrolysis in an acid medium (100 mg of particles in 5 ml of a 1:1 mixture of $HCl:HNO_3$). 1 ml of the solution was then placed in a 10 ml volumetric flask to which 2 ml of a solution of hydroxylamine HCl (1.4 M), 5 ml of acetate buffer (2 M) and 2 ml of 1,10-phenanthroline (5 mM) were added. After 20 min, and orangey-red complex forms, the absorbance of which at 510 nm is measured by spectrophotometry (Shimadzu, France) against a blank which does not contain iron. The absorbance at 510 nm is proportional to the amount of iron. More particularly, the amount of zinc was assayed using a method described by M. Khoder et al. [7] and M. Arvand et al. [8]. The CH—Zn particles were first subjected to hydrolysis in an acid medium (100 mg of particles in 5 ml of a 1:1 mixture of HCl:$HNO_3$). 1 ml of the solution was then placed in a 10 ml volumetric flask to which 1 ml of an ammonia buffer (1 M, pH=10) and 3 ml of 1-(2-pyridylazo)-2-naphthol (PAN) ($5 \times 10^{-4}$ M) in ethanol were added. The volume is then made up to 10 ml with ethanol. The flask is then stirred and placed in a thermostated bath at 40° C. for 10 min in order to obtain the formation of the PAN-Zn complex. The absorbance at 550 nm is then measured with a Shimadzu spectrophotometer (France) against a blank; it is proportional to the amount of zinc.

Example 3

Study of the Adsorption of an Undesirable Molecule

The particles (1 mg/ml) were incubated at 37° C. in a simulated colonic medium consisting of HEPES buffer (10 mM) and NaCl (145 mM) containing 5200 pg/ml of pectinolytic enzymes (Pectinex, Sigma-Aldrich) containing ciprofloxacin at a concentration of 400 μg/ml, and the pH was adjusted to 5.5 with NaOH (1N). The kinetics of adsorption of the ciprofloxacin by the crosslinked particles of chitosan (control), of chitosan-Cu, of chitosan-Fe(II), of chitosan-Fe (III) and of chitosan-Zn were evaluated for five hours (FIG. 4).

For the chitosan particles, chitosan-Cu particles and chitosan-Fe(II) particles, the adsorption plateau is reached rapidly (30 minutes) and is at 50, 25 and 100 μg, respectively.

The adsorption plateau is reached less rapidly for the chitosan-Zn and the chitosan-Fe(III): 5 hours and 3 hours, respectively. The amount of ciprofloxacin adsorbed by the chitosan-Zn and the chitosan-Fe(III) is 350 μg, i.e. almost as much as active carbon (400 μg) which is considered to be a good but nonspecific adsorbent. The chitosan-Zn particles and chitosan-Fe(III) particles can therefore be considered to be adsorbents that are particularly efficient with respect to ciprofloxacin.

Example 4

Study of the Adsorption Specificity

The specific adsorption of fluoroquinolones by the particles of the invention is carried out. Chitosan-Fe(III) particles (1 mg/ml) are incubated at 37° C. in a simulated colonic medium identical to that described in example 3, but containing hydrocortisone, at the same concentration as the ciprofloxacin in example 3, i.e. 400 μg/ml.

Whereas ciprofloxacin is adsorbed in an amount of approximately 350 μg by the chitosan-Fe(III) particles, hydrocortisone is weakly adsorbed by the chitosan-Fe(III) particles: 50 μg<(FIG. 5). On the other hand, active carbon (1 mg/ml) leads to a strong adsorption of hydrocortisone. These results confirm the specificity of the particles according to the invention for fluoroquinolones.

Example 5

Competition between Ciprofloxacin and Nimesulide

The specific adsorption of a fluoroquinolone, ciprofloxacin, by the particles of the invention is carried out under conditions of competition with nimesulide. Chitosan-Fe(III) particles and chitosan-Zn particles (1 mg/ml) are incubated at 37° C. in a simulated colonic medium identical to that described in example 3 containing nimesulide (100 μg/ml) and ciprofloxacin (400 μg/ml). For this example, the pH was adjusted to 6.

Whereas ciprofloxacin is adsorbed in an amount of approximately 350 μg by the chitosan-Zn particles and in an amount of 100 μg for the chitosan-Fe (III) particles, nimesulide is weakly adsorbed by the two types of particles: 10 μg<(FIG. 6). These results confirm the specificity of the particles according to the invention for fluoroquinolones.

Example 6

Particle Encapsulation

Pectin, a natural polysaccharide (extracted from citrus fruit, citrus family), is used in its amidated (19 to 23%) and weakly methylated (22 to 28%) form. It is obtained from Cargill (Belgium) under the trade name Unipectine OG175C.

Preparation of Beads not Containing Particles

Beads not containing particles are prepared by introducing, dropwise, through a nozzle with an internal diameter of 0.8 mm, an aqueous solution of pectin at a concentration of from 1 to 10% (w/v) in a solution of a zinc salt such as zinc acetate (0.5 to 12% (w/v)) or a calcium salt such as calcium chloride (0.5 to 12% (w/v)), so as to form beads of zinc pectinate or calcium pectinate. The beads obtained are recovered after a residence time of 30 min in the counterion bath. The beads thus obtained are then recovered by filtration, rinsed three times for 1 min with ultrapure water (conductivity 18.2 MegaOhms·cm, Synergy purification system from Millipore, France) in order to remove the divalent ions which do not participate in the network, in an incubator at 37° C. for 12 hours.

Preparation of Beads Containing Particles

The preparation of beads containing chitosan particles or chitosan-metal particles is slightly different (FIG. 7). The particles are suspended in water at a concentration of 4% (w/v). A solution of pectin at 4% (w/v) is then added to the suspension in an equal volume and the whole mixture is mixed by means of a vortex stirrer (sold for example by the company VWR) or with a blade, for example helicoidal, stirrer. The beads containing the particles are then formed by introducing, dropwise, through a nozzle with an internal diameter of 0.8 mm, the mixture of pectin/particles in a solution of a zinc salt such as zinc acetate (0.5 to 12% (w/v)) or a calcium salt such as calcium chloride (0.5% to 12% (w/v)), so as to form zinc pectinate beads or calcium pectinate beads (FIG. 7). The beads obtained are recovered after a residence time of 30 min in the counterion bath. The beads thus obtained are then recovered by filtration, rinsed three times for 1 min with ultrapure water (conductivity 18.2 megaohms·cm, Synergy purification system from Millipore, France) in order to eliminate the divalent ions which do not participate in the network, and dried in an incubator at 37° C. for 12 hours. The electrostatic interactions between the carboxylate groups of pectin and amine groups of the chitosan lead to gelling of the pectin/particles mixture. The gelling time depends on the initial concentration of the two components.

Pectin Beads Containing Chitosan-Fe(III)

Because of the gelling problems, for a final pectin concentration in the mixture of 3% (w/v), it is possible to formulate spherical beads containing up to 1.5% (w/v) of chitosan-Fe (III). For a final pectin concentration in the mixture of 2.5% (w/v), it is possible to formulate spherical beads containing up to 2.5% (w/v) of chitosan-Fe(III). For a final pectin concentration in the mixture of 2% (w/v), it is possible to formulate spherical beads containing up to 2% (w/v) of chitosan-Fe(III). For a final pectin concentration in the mixture of 1.5% (w/v), it is possible to formulate spherical beats containing up to 2.5% (w/v) of chitosan-Fe(III). Above these particle concentrations, the suspension may become too viscous and worm-like micelles may be obtained.

Pectin Beads Containing Chitosan-Zn

For a final pectin concentration in the mixture of 1.5% (w/v), it is possible to formulate spherical beads containing up to 0.5% chitosan-Zn. Above these particle concentrations, the suspension may become too viscous and worm-like micelles may be obtained. With the chitosan-Zn, the Zn ions participate in the gelling of the pectin.

The observation of the beads by optical and electron microscopy shows particles of spherical shapes, of quite homogeneous sizes between 1 and 1.3 mm and of a mass which ranges from 1 to 2 mg. A uniform dispersion of the chitosan-metal particles and also a rough surface are observed by scanning electron microscopy.

Example 7

Study of the Adsorption of an Undesirable Molecule

The beads of zinc pectinate encapsulating chitosan-metal particles were incubated in the simulated intestinal medium (SIM) containing 400 µg/ml of ciprofloxacin for five hours. The simulated intestinal medium is an aqueous solution of HEPES buffer (30 mM) containing 1% of pancreatin (w/v); the pH is adjusted to 6.8 with 0.2 M NaOH. The beads swell but remain intact at the end of these five hours of incubation. It was nevertheless observed that a part of the ciprofloxacin in the SIM was adsorbed: approximately 100 to 120 µg after five hours (FIG. 9).

After preincubation in the SIM containing ciprofloxacin, the beads retain their adsorbent capacity since up to 330 µg of ciprofloxacin in the simulated colonic medium (SCM, described above) is adsorbed (FIG. 10).

If the amounts of ciprofloxacin in the SIM and in the SCM that are adsorbed are added together, it can be found that the equivalent in beads of 1 mg of chitosan-Fe(III) particles succeeds in adsorbing approximately 350 µg of ciprofloxacin, that is to say what had been obtained for the non-encapsulated particles. The encapsulation of the particles in the zinc pectinate beads does not therefore modify their adsorbent capacity.

Example 8

Coating of the Encapsulated Particles

In order to limit the adsorption in the simulated intestinal medium (SIM), the dry beads were coated with 5% (w/w) of Eudragit® RS. For this, 5 g of Eudragit® RS and 1 g of PEG 300 (Sigma-Aldrich) are dissolved in 300 ml of an acetone/ethanol mixture (2/1, v/v). The solution is then spray-dried by means of a manual spray drier onto the dry beads kept rotating at 20 rpm in a miniturbine heated to 37° C. with a hot-air gun (Steinel, Radiospares, France). The weight increase of from 5 to 10% was verified by weighing. The homogeneity of the coating is verified by scanning electron microscopy (FIG. 8).

The incubation of the coated beads in the SIM described above at 400 µg/ml of ciprofloxacin shows that Eudragit® RS makes it possible to limit the adsorption of ciprofloxacin: 25-30 µg instead of 100 to 120 µg for the uncoated beads (FIG. 11). This layer of Eudragit does not modify the adsorbent capacity of the beads: after preincubation in the SIM, the coated beads can still adsorb 300 µg of ciprofloxacin (FIG. 12).

LIST OF REFERENCES

[1] Bartlett J. G., New England Journal of Medicine, 346, p. 334-339, 2002.
[2] Holmberg S. D. et al., New England Journal of Medicine, 311, 617, 1984.
[3] Bartlett J. G., *Clostridium difficile* infection: pathophysiology and diagnosis. Seminar in Gastrointestinal Disease 8, 12, 1997.
[4] Broussignac, P. Chim. Ind. Gén. Chim., no. 99, p. 1241-1246, 1968.
[5] Médicaments et environnement [Drugs and environment]-report by the Academie Nationale de Pharmacie [National Academy of Pharmacy], p. 23/103-25/103, September 2008.
[6] K. C. Gupta et al., Carbohydrate Polymers, 66, p. 43-45, 2006; K. C. Gupta et al., Carbohydrate Research, 342, p. 2244-2252, 2007.
[7] M. Khoder et al., International Journal of Pharmaceutics, 379, p. 251-259, 2009.
[8] M. Arvand et al., J. Anal. Chem., 62, p. 342-347, 2007.
[9] I. El-Gibaly, International Journal of Pharmaceutics, 232, p. 199-211, 2002.

The invention claimed is:

1. A galenic form comprising particles capable of specifically adsorbing undesirable molecules present in the digestive tract, said particles comprising (i) a cationic polymer comprising chitosan, associated with (ii) at least one metal ion selected from the group consisting of iron, copper, zinc, and mixtures thereof, said cationic polymer and said at least one metal ion forming a complex, wherein the particles are encapsulated in pectin beads.

2. The galenic form according to claim 1, wherein the chitosan has a degree of deacetylation of at least 50%.

3. The galenic form according to claim 1, wherein, for 1 g of cationic polymer, an amount of the at least one associated metal ion is from 1 to 300 mg.

4. The galenic form according to claim 3, wherein, for 1 g of chitosan, the amount of the at least one associated metal ion is from 20 to 200 mg.

5. The galenic form according to claim 1, wherein the particles have a diameter ranging from 0.01 µm to 1 mm.

6. The galenic form according to claim 1, wherein the particles are configured to specifically adsorb undesirable molecules selected from the group consisting of:
domestic toxic substances;
medicine residues or the metabolites of medicines which are intentionally and/or accidentally ingested;

medicine residues or the metabolites of the medicines most widely used in human or veterinary medicine that may be found in water; and
residual antibiotics.

7. The galenic form according to claim 6, wherein the particles are configured to adsorb residual antibiotics selected from the group consisting of quinolones, aminoglucosides, beta-lactam antibiotics, macrolides, sulfamides, antitubercular agents and tetracyclines.

8. The galenic form according to claim 6, wherein the undesirable molecules are residual antibiotics selected from the group consisting of quinolones, aminoglucosides, beta-lactam antibiotics, macrolides, sulfamides, antitubercular agents and tetracyclines, and the particles further contain at least one agent capable of inactivating said antibiotics.

9. The galenic form according to claim 8, wherein the at least one agent capable of inactivating the antibiotics is an enzyme.

10. The galenic form according to claim 1, wherein the particles have a degree of crosslinking ranging from 0 to 100%.

11. The galenic form according to claim 1, wherein the pectin beads are zinc pectinate beads or calcium pectinate beads.

12. The galenic form according to claim 1, wherein a concentration of pectin is from 5 to 95% by weight, relative to the total weight of the galenic form, and that of the particles comprising associated cationic polymer-metal ion(s) is from 5 to 95% by weight, relative to the total weight of the galenic form.

13. The galenic form according to claim 1, wherein the pectin beads are spherical in shape and have a diameter ranging from 0.2 to 3 mm.

14. The galenic form according to claim 1, wherein the particles are coated with a polymer selected from the group consisting of:
  a cationic polymer selected from the group consisting of polyethyleneimines, polylysines, polyarginines, DEAE dextran and chitosan;
  a cellulosic polymer selected from the group consisting of hydroxypropylcellulose, hydroxyethylcellulose, hydroxymethylcellulose, hydroxypropylmethylcellulose, hydroxypropylmethylcellulose acetate succinate, hydroxypropylmethylcellulose phthalate, methylcellulose, ethylcellulose, cellulose acetate, cellulose acetate phthalate, cellulose acetate trimellitate, and sodium carboxymethylcellulose;
  a polymer of acrylic acid, of methacrylic acid, of ethyl acrylate, of ethyl acrylate, of methyl methacrylate and/or of ethyl methacrylate,
  a vinyl polymer selected from the group consisting of polyvinylpyrrolidone, vinyl acetate, vinyl acetate phthalate, vinyl acetate-crotonic acid, and ethylene-vinyl acetate.

15. A method for preparing a galenic form according to claim 1, wherein:
  (a) a cationic polymer comprising chitosan is dissolved in an aqueous solution of a metal salt or of a mixture of metal salts, under pH conditions <7, advantageously at a pH of between 1 and 6.8, even more advantageously at a pH between 1.2 and 6, in such a way that the metal ions of said salt or said mixture of salts associate with said cationic polymer so as to form a complex;
  (b) the solution obtained in (a) is subjected to spray-drying, so as to obtain particles of said complex;
  (c) crosslinking of the particles obtained in step (b) is optionally carried out in an organic solvent in the presence of a crosslinking agent.

16. A medicine comprising the galenic form according to claim 1.

17. A method of treating undesirable effects linked to an imbalance of the intestinal flora and/or colic following treatment with antibiotics, comprising administering to a patient in need thereof a galenic form according to claim 1, as a medicine.

* * * * *